United States Patent [19]

Ayres et al.

[11] 4,327,227

[45] Apr. 27, 1982

[54] PROCESS FOR PRODUCING PURIFIED BROMINATED AROMATIC COMPOUNDS

[75] Inventors: James T. Ayres; David L. McAllister, both of El Dorado, Ark.; John L. Sands, West Lafayette, Ind.

[73] Assignee: Great Lakes Chemical Corporation, West Lafayette, Ind.

[21] Appl. No.: 163,957

[22] Filed: Jul. 8, 1980

Related U.S. Application Data

[63] Continuation-in-part of Ser. No. 122,860, Feb. 20, 1980, abandoned, which is a continuation of Ser. No. 926,934, Jul. 21, 1978, abandoned, which is a continuation of Ser. No. 784,235, Apr. 4, 1977, abandoned.

[51] Int. Cl.$^3$ ............................................. C07C 41/22
[52] U.S. Cl. ..................................... 568/639; 570/211
[58] Field of Search ....................... 568/639; 570/211

[56] References Cited

U.S. PATENT DOCUMENTS

| | | | |
|---|---|---|---|
| 2,022,634 | 11/1935 | Britton et al. | 568/639 |
| 3,733,366 | 5/1973 | Burk | 570/211 |
| 3,752,856 | 8/1973 | Nagy et al. | 568/639 |
| 3,833,674 | 9/1974 | Brackenridge | 568/639 X |
| 3,965,197 | 6/1976 | Stepniczka | 570/211 X |

FOREIGN PATENT DOCUMENTS 1472383 5/1977 United Kingdom ................ 568/639

OTHER PUBLICATIONS

Coulson et al., Chemical Engineering, vol. II, (1955), p. 867.

*Primary Examiner*—Bernard Helfin
*Attorney, Agent, or Firm*—Kirkland & Ellis

[57] ABSTRACT

Highly purified brominated aromatic compounds such as decabromodiphenyl ether, pentabromophenol, and the like may be obtained by grinding the crude brominated product to provide particles predominantly less than about 20 microns in diameter and thereafter heating the crude ground brominated product for a time and at a temperature in order to effect substantial removal of the bromine and hydrogen bromide impurities therefrom. Optionally, the product may be ground a second time after the heating step to optimize product particle size and liberate residual impurities. The foregoing procedure is especially effective where the brominated compound is a thermally stable solid under the conditions of treatment and is substantially free from impurities containing aliphatic and alicyclic hydrocarbon groups.

16 Claims, No Drawings

PROCESS FOR PRODUCING PURIFIED BROMINATED AROMATIC COMPOUNDS

CROSS-REFERENCE

This application is a continuation-in-part of applicants' co-pending application, Ser. No. 122,860, filed Feb. 20, 1980, now abandoned, which was a continuation of applicants' prior application, Ser. No. 926,934, filed July 21, 1978, now abandoned, which was in turn a continuation of applicants' original application, Ser. No. 784,235, filed Apr. 4, 1977, now abandoned.

BACKGROUND OF THE INVENTION

1. Field of the Invention

This invention relates to the purification of brominated aromatic compounds such as decabromodiphenyl ether and pentabromophenol and more particularly to a process for purifying aromatic compounds containing residual free bromine and by-product hydrogen bromide.

2. Description of the Prior Art

High levels of purity are required for brominated aromatic compounds which have found utility as flame retardant agents in polymer compositions. In particular, it is important that such brominated products have extremely low levels of residual impurities such as free bromine, hydrogen bromide, retained catalysts, by-product bromine containing derivatives and the like since the presence of such impurities can have undesirable effects on the polymer compositions in which such agents are used. Purity is particularly important from the standpoint of color, and thermal stability under the processing conditions in commercial molding operations is likewise an essential parameter.

High purity is an especially important consideration in the case of decabromodiphenyl ether, a flame retardant agent that has found wide application as an additive for high impact polystyrene used in television cabinets and other consumer appliances.

The preparation of decabromodiphenyl ether by the direct bromination of diphenyl oxide using excess bromine itself as a reaction solvent, as disclosed in British patent specification No. 1,411,524, published Oct. 29, 1975, and in Stepniczka, U.S. Pat. No. 3,965,197, issued June 22, 1976, produces highly brominated derivatives containing undesirably large amounts of occluded free bromine and by-product hydrogen bromide.

The cited British specification describes the use of various chemical purification treatments (e.g., injection of sulfur dioxide to convert occluded bromine into hydrobromic acid and injection of ethylene to convert residual bromine into dibromoethane). The cited U.S. patent merely describes the recovery of crude brominated product and gross separation of bromine therefrom by injecting superheated steam and by washing with hot dilute hydrochloric acid and hot water. The patent does not describe purification of the crude reaction project.

Traditional purification methods such as recrystallization techniques are usable only with difficulty with materials such as decabromodiphenyl ether because its limited solubility in available solvents makes recrystallization both cumbersome and uneconomical.

Burk, U.S. Pat. No. 3,733,366, granted May 15, 1973, describes a procedure for decolorizing brominated biphenyl obtained by treating biphenyl with bromine or bromine chloride in methylene chloride solvent in the presence of aluminum chloride catalyst. The patentee describes heating the product to a temperature between about 100° C. and about 160° C. with a preferred temperature range being about 110° C. to about 150° C. (Col. 2 lines 7-13). The disclosed heating step may take place optionally in the presence of solvents such as ethylene dibromide, toluene and xylenes. The patent is concerned only with decolorizing brominated biphenyl and contains no disclosure that would aid one in purifying materials such as decabromodiphenyl ether using a heat treating step.

Britton, U.S. Pat. No. 2,022,634, issued Nov. 26, 1935 relates to the halogenation of diphenyl oxide and describes (page 2, col. 1, lines 3-7) heating the reaction mixture to above 75° C., preferably between 250° and 350° C., to destroy bromine addition products. Britton's products are not completely brominated, nor does the patentee recognize that free bromine, rather than bromine addition products, may be removed by such a heating step.

Nagy et al, U.S. Pat. No. 3,752,856, issued Aug. 14, 1973, is directed to a process for producing brominated compounds in which an intimate mixture between bromine and the organic starting material is obtained by physical mixing with a sigma type blender. After bromination, the apparatus is flushed with dry air, preferably under lowered pressure, to remove the residual hydrobromic acid and, if applicable, excess bromine, and the whole mass is allowed to cool while continuing the grinding operation. The brominated aromatic product is said to be removed in the form of a powder as a rule. (Column 3, lines 5-11).

The patentee suggests that gaseous ammonia be passed into the apparatus to neutralize "the hydrobromic acid and possibly the bromine retained by the product" and goes on to describe purification of "[t]he crude product" by "washing with acidified water or better still, by wet grinding in the presence of a dilute inorganic acid, followed by washing with water and by drying." The reference also suggests that "[r]ecrystallization in an appropriate solvent offers another possibility of purification."

Nagy et al's Example III is a preparation of decabromodiphenyl in which the crude product was "heated at the temperature of 200° C. under normal pressure and under a nitrogen flow . . . ," the resulting product containing over 2 weight percent ammonium and aluminum bromide impurities. In Example IX of the patent, crude decabromodiphenyl was first subjected to dry air at 70° C. under vacuum (20 mm Hg) followed by heating at 150°-200° C. "under a flow of air." Recovery was completed by washing the "crude product" with aqueous NaOH. In Example IV, which is directed to decabromodiphenyl ether, purification is carried out by recrystallization in chlorobenezene.

Brackenridge, U.S. Pat. No. 3,833,674, issued Sept. 3, 1974, describes a process for polybromination of aromatic compounds including diphenyl ether by reacting an aromatic compound with bromine in the presence of methylene bromide solvent. The patent states (column 2, lines 11-15) that "a main improvement" of the invention is the isolation of the product by precipitation from the reaction mixture by adding methanol or the like as a precipitant.

Brackenridge describes four approaches to enhancement of product purity. (Column 4, line 46, et seq.) More particularly, the patent suggests the exclusion of light from the methylene bromide and methanol and from the reaction and recovery steps, minimization of temperature, and use of distilled solvent and precipitating agent. (Id., lines 60–68).

As a result, the prior art has failed totally to appreciate the applicability of the techniques of the present invention to the purification of brominated aromatic compounds such as decabromodiphenyl ether. In particular, the prior art has failed to recognize the importance of the crude decabromodiphenyl ether being thermally stable, much less that thermal stability is directly controlled by the substantial exclusion of aliphatic and alicyclic hydrocarbon impurities from the raw materials employed. The art further fails to disclose the importance of precise particle size control of the brominated aromatic product to be subjected to the heating step in achieving desired elimination of bromine, bromide, and other impurities.

Accordingly, it is a primary object of this invention to obtain a process for producing purified brominated aromatic compounds that is superior to the techniques that heretofore have been employed.

Another object is to provide a method of the character described that may be economically employed in purifying decabromodiphenyl ether.

A still further object is to provide a method of obtaining thermally stable decabromodiphenyl ether that may be purified in accordance with the present invention.

SUMMARY OF THE INVENTION

The foregoing and other objects, advantages, and features of the present invention may be achieved with a process for purifying crude brominated aromatic compounds such as decabromodiphenyl ether comprising the steps of grinding the crude decabromodiphenyl ether to provide particles predominantly less than about 20 microns in diameter and substantially entirely less than about 100 microns in diameter and thereafter heating the crude, ground decabromodiphenyl ether at a temperature of about 150°–300° C. for a time sufficient to effect substantial removal of the impurities therefrom.

Advantageously, the purified decabromodiphenyl ether is subjected to an optional final grinding step after heating in order to reduce the size of the particles (which may agglomerate somewhat during the heating step). In addition to providing a purified product having a more acceptable particle size, the second grinding step also serves to reduce impurity levels further, especially where the combination of grinding and heating initially employed does not attain the desired degree of purification.

It has further been found that the foregoing procedure is especially effective when employed with thermally stable decabromodiphenyl ether obtained by direct bromination of diphenyl oxide in an excess of bromine without other reaction solvents being present and in the presence of a bromination catalyst. Such thermally stable decabromodiphenyl ether may be obtained by substantially excluding impurities containing aliphatic and alicyclic hydrocarbon groups from the diphenyl oxide and bromine.

DETAILED DESCRIPTION OF THE PREFERRED EMBODIMENTS

Unpurified, crude decabromodiphenyl ether ("DBDPE") produced by the direct bromination of diphenyl oxide ("DPO"), also known as diphenyl ether, in an excess of bromine without other reaction solvents being present and in the presence of a bromination catalyst is typically light yellow-orange in color, contains about 300–1000 parts per million occluded free bromine and in excess of 400 parts per million occluded hydrogen bromide, and has poor thermal stability. For reasons well known in the art, it is highly desirable to remove occluded bromine, hydrogen bromide, and other impurities before using the decabromodiphenyl ether as a flame retardant agent in high impact polystyrene and other polymers.

Although the crude product could be purified by multiple recrystallizations from an appropriate solvent, the material is so insoluble in known solvents, that purification by recrystallization is uneconomical and impractical.

In accordance with this invention it has been found that crude decabromodiphenyl ether, especially thermally stable crude decabromodiphenyl ether, may be readily purified with assurance by grinding the crude decabromodiphenyl ether to provide particles predominantly less than about 20 microns in diameter and substantially entirely less than about 100 microns in diameter. Thereafter, the crude ground decabromodiphenyl ether is heated at a temperature of about 150°–300° C. for a time sufficient to effect substantial removal of the impurities therefrom. Advantageously, the purified decabromodiphenyl ether is subjected to an optional final grinding step to reduce the size of the particles.

Thermal Stability

An important parameter in obtaining decabromodiphenyl ether of the desired purity is the thermal stability of the material. By thermally stable it is meant that the crude decabromodiphenyl ether can be heated to a temperature of about 250°–300° C. without significant discoloration. The desired thermally stable crude decabromodiphenyl ether is obtained by the direct bromination of diphenyl oxide with an excess of bromine without other reaction solvent being present, employing catalysts such as iron, iron halides, aluminum, aluminum halides and the like. It is critically important in obtaining the desired thermally stable decabromodiphenyl ether that highly purified bromine and diphenyl oxide be employed. In particular, impurities containing aliphatic and alicyclic hydrocarbon groups must be substantially excluded from the bromine and diphenyl oxide.

In the case of diphenyl oxide, the presence of common impurities such as dibenzofuran and 2-phenylphenol may be tolerated at levels as high as 5000 parts per million. Other possible diphenyl oxide impurities such as methylated diphenyl ether derivatives (e.g., 4-methyldiphenyl ether and 3,5-dimethyldiphenyl ether) adversely affect thermal stability of the decabromodiphenyl ether produced therefrom. The latter result is believed to arise from the presence of aliphatic groupings on the molecule which, when brominated, yield thermally unstable aliphatic compounds.

In the case of bromine, it has been found that the material must be essentially free from hydrocarbons and should contain low levels of chloroform and carbon tetrachloride. Typical production bromine contains significant levels of hydrocarbon oils, and it is desirable to reduce their content to 5 parts per million or less in order to achieve the desired thermally stable decabromodiphenyl ether.

During the bromination of decabromodiphenyl ether, impurities such as chloroform and carbon tetrachloride appear to be converted to bromoform and carbon tetrabromide which have a small detrimental effect on thermal stability of decabromodiphenyl ether.

The hydrocarbon oil impurities normally found in production bromine are high boiling materials that can be eliminated by distillation, with the resultant bromine containing water, chloroform, and carbon tetrachloride as the only significant impurities.

Alternatively, bromine that is essentially free of organic contaminants may be prepared by treating impure bromine with aluminum metal or aluminum chloride followed by distillation. The aluminum treatment converts the chloroform and carbon tetrachloride to higher boiling bromoform and carbon tetrabromide which can be separated along with the oily hydrocarbons by simple bromine distillation. If this material is fractionated with a high reflux ratio, bromine containing water as essentially the only impurity is obtained.

Grinding

As noted, crude decabromodiphenyl ether is preferably ground by convenient means such that the particles are predominantly less than about 20 microns in diameter and substantially entirely less than 100 microns in diameter.

The term "predominantly" is used herein to mean that a substantial proportion of the particles (i.e., about 50% or more by weight) are less than the specified diameter (e.g., 20 microns) but that appreciable amounts (e.g., up to about 50% by weight) of larger particles may be present consistent with the objectives of this invention. In accordance with this invention, particle size determinations have been made using a Model PA-II Coulter Counter particle size analyzer (available from Coulter Electronics, Inc., Hialeah, Fla.) employing 30 to 70 micron apertures. These determinations have also been verified by microscopic visual observations. All percentages specified herein are by weight unless otherwise noted.

Grinding may be performed by any suitable grinding equipment such as an air mill, sand mill, ball mill, hammer mill or the like. Air milling procedures have been shown to be especially effective for large scale grinding of crude decabromodiphenyl ether in accordance with this invention.

The following Examples demonstrate the grinding of crude decabromodiphenyl ether in accordance with this invention.

EXAMPLE I

Crude DBDPE was ground in a commercial air mill operated so as to produce a wide range of particle sizes. Microscopic examination revealed particles from less than 0.5 microns up to 100 microns in diameter. About 3.9% of the particles were greater than 45 microns (325 mesh). The particle size distribution, as determined by Coulter Counter analysis, is given in Table I.

TABLE I

| Particle Size Analysis-Example I DBDPE | | |
|---|---|---|
| Particle Size Range (Microns) | Wt % of Sample 70 μ Aperture | Wt % of Sample 30 μ Aperture |
| 0.63–0.79 | | 4.3 |
| 0.79–1.00 | | 4.9 |
| 1.00–1.26 | | 4.6 |
| 1.26–1.59 | 8.0 | 6.5 |
| 1.59–2.00 | 8.2 | 7.5 |
| 2.00–2.52 | 7.7 | 8.4 |
| 2.52–3.17 | 8.8 | 8.3 |
| 3.17–4.00 | 8.9 | 8.5 |
| 4.00–5.04 | 9.2 | 8.7 |
| 5.04–6.35 | 8.5 | 6.8 |
| 6.35–8.00 | 8.2 | 8.2 |
| 8.00–10.1 | 8.0 | 6.7 |
| 10.1–12.7 | 6.7 | 7.2 |
| 12.7–16.0 | 5.7 | 7.5 |
| 16.0–20.2 | 4.0 | 5.0 |
| 20.2–25.4 | 2.8 | |
| 25.4–32.0 | 3.0 | |
| 32.0–40.3 | 1.0 | |

| Aperture Size (Microns) | 50 wt % <Microns | 90 wt % <Microns |
|---|---|---|
| 30 | 4.0 | 13.5 |
| 70 | 5.0 | 17.5 |

Crude ground DBDPE obtained in accordance with this Example contains particles that are predominantly less than about 20 microns in diameter and substantially entirely less than 100 microns in diameter and is referred to herein as "Ground DBDPE" or "Example I DBDPE."

EXAMPLE II

Crude DBDPE was ground in an air mill to produce particles substantially entirely less than 20 microns in diameter. Microscopic observation showed a broad distribution of particles from 1–10 microns, numerous particles in the 5–10 micron range and a few particles in the 20–50 micron range. The particle size distribution, as determined by Coulter Counter analysis, is given in Table II.

TABLE II

| Particle Size Analysis-Example II DBDPE | | |
|---|---|---|
| Particle Size Range (Microns) | Wt % of Sample 70 μ Aperture | Wt % of Sample 30 μ Aperture |
| 0.63–0.79 | | 3.2 |
| 0.79–1.00 | | 4.0 |
| 1.00–1.26 | | 4.3 |
| 1.26–1.59 | 7.0 | 6.3 |
| 1.59–2.00 | 8.5 | 7.6 |
| 2.00–2.52 | 8.8 | 8.6 |
| 2.52–3.17 | 10.3 | 8.8 |
| 3.17–4.00 | 10.7 | 9.9 |
| 4.00–5.04 | 10.5 | 11.0 |
| 5.04–6.35 | 10.8 | 9.3 |
| 6.35–8.00 | 10.8 | 7.6 |
| 8.00–10.1 | 9.3 | 7.7 |
| 10.1–12.7 | 8.2 | 7.5 |
| 12.7–16.0 | 3.3 | 5.3 |
| 16.0–20.2 | 1.3 | |
| 20.2–25.4 | 0 | |
| 25.4–32.0 | 0.8 | |
| 32.0–40.3 | | |

| Aperture Size (Microns) | 50 Wt % <Microns | 90 Wt % <Microns |
|---|---|---|
| 30 | 3.9 | 11.5 |
| 70 | 4.5 | 11.5 |

The DBDPE particles obtained in accordance with this Example are predominantly less than about 4 microns in diameter, with at least about 90% of the particles being less than about 15 microns in diameter and with the particles being substantially entirely less than 20 microns in diameter. Crude ground DBDPE meeting these particle size criteria is preferred in accordance with this invention and is referred to herein as "Fine DBDPE" or "Example II DBDPE."

EXAMPLE III

Crude DBDPE was passed three times through an air mill so as to obtain very finely ground DBDPE. Microscopic evaluation showed most particles to be less than 5 microns in diameter, with larger particles lying in the 10 to 15 micron range. The Coulter Counter particle size analysis is given in Table III.

TABLE III
Particle Size Analysis-Example III DBDPE

| Particle Size Range (Microns) | Wt % of Sample 70 μ Aperture | Wt % of Sample 30 μ Aperture |
|---|---|---|
| 0.63–0.79 | | 4.6 |
| 0.79–1.00 | | 6.5 |
| 1.00–1.26 | | 7.3 |
| 1.26–1.59 | 15.5 | 12.9 |
| 1.59–2.00 | 17.4 | 16.4 |
| 2.00–2.52 | 15.5 | 18.1 |
| 2.52–3.17 | 14.9 | 14.7 |
| 3.17–4.00 | 11.6 | 8.9 |
| 4.00–5.04 | 9.2 | 6.4 |
| 5.04–6.35 | 6.2 | 4.2 |
| 6.35–8.00 | 4.4 | 2.0 |
| 8.00–10.1 | 3.2 | 0.6 |
| 10.1–12.7 | 1.0 | 0 |
| 12.7–16.0 | 0.5 | 0 |
| 16.0–20.2 | 0 | |
| 20.2–25.4 | | |
| 25.4–32.0 | | |
| 32.0–40.3 | | |

| Aperture Size (Microns) | 50 Wt % <Microns | 90 Wt % <Microns |
|---|---|---|
| 30 | 2.1 | 4.5 |
| 70 | 2.7 | 6.2 |

Very finely ground DBDPE obtained in accordance with Example III has particles that are predominantly less than 3 microns in diameter, at least about 90% being less than 5 microns in diameter and the particles being substantially entirely less than about 15 microns in diameter. Crude ground DBDPE meeting these criteria is especially preferred and is referred to herein as "Very Fine DBDPE" or "Example III DBDPE".

EXAMPLE IV

For comparative purposes, crude DBDPE taken directly from the product recovery filter was examined microscopically. This examination revealed that essentially all particles were less than 100 microns in diameter, with most particles lying in the 30–60 micron range and very few particles being less than 30 microns. Other filter samples have been observed to have large numbers of particles in the 100–300 micron range. Unground material of the type observed in this Example is referred to herein as "Unground DBDPE" or "Example IV DBDPE."

Heating

The crude, ground decabromodiphenyl ether is heated for a time and at a temperature so as to effect substantial removal of the free bromine, bromide, and other impurities therefrom. The minimum temperature that permits the benefits of this invention to be achieved is about 150° C. Desirably, however, the ground material is heated at a temperature of least about 175° C. and preferably at least about 200° C.

There is no convenient maximum heating time although significant benefits are ordinarily not achieved with heating times longer than about one hour. Decabromodiphenyl ether melts at temperatures in excess of 300° C., and thus a convenient maximum temperature in accordance with this invention is thus about 300° C., preferably about 275° C.

Generally, heating times and temperatures are inversely related. Thus, for shorter heating times, generally higher heating temperatures must be employed (and vice versa) to reach the same degree of impurity removal. Similarly, the degree of comminution during the grinding step affects the times and temperatures that must be employed.

Thus, for Example I DBDPE (i.e., material which is relatively coarsely ground), the minimum heating times and temperatures required to achieve the purification objectives of this invention are generally longer and/or higher than is the case for Example II or III DBDPE. Thus, Example I DBDPE should be heated for at least about one hour at a temperature of at least about 250° C.

However, when a more finely ground DBDPE is purified in accordance with this invention, somewhat lower minimum heating temperatures are required. Thus, Example II DBDPE need only be heated at a temperature of at least about 225° C. for at least about 30 minutes.

Very fine decabromodiphenyl ether (i.e., Example III DBDPE) need be heated only to a temperature of at least about 175° for 30 minutes or more. Indeed, Very Finely DBDPE may even be purified by heating at temperatures as low as 150° C. for about 4 hours or longer.

Conversely, where higher temperatures are used, the heating times may be significantly reduced. Thus, where Fine DBDPE is heated at a temperature of 275° C., the heating time is about 10 minutes or less, and Very Fine DBDPE may be purified in about 2 minutes by heating at 275° C.

Grinding is an essential feature of the process of this invention because even prolonged heating at 275° C. is incapable of satisfactorily purifying Unground (Example IV) DBDPE.

To summarize, Ground (Example I) DBDPE should be heated at temperatures in the range of about 250°–300° C. for at least about 1 hour. Fine (Example II) DBDPE should be heated at a temperature in the range of about 225°–300° C. for about 10–30 minutes or more, and Very Fine (Example III) DBDPE should be heated at a temperature in the range of about 150°–300° C. for about 2 minutes to 4 hours.

Thus, in general 150°–300° C. is the temperature range for practicing this invention, and about 2 minutes up to 4 hours or more is the heating time period. Longer heat times may be used but with little additional benefit.

Preferably, the heating temperature is about 200°–275° C., with about 210°–260° C. being an especially preferred range. Preferred heating times lie in the range of about 5 minutes to 1 hour, especially about 10–45 minutes.

Subsequent Grinding

Desirably, the purified heated ground decabromodiphenyl ether is subjected to an additional grinding step after heating. The objective of the subsequent grinding is to ensure that the particles in the purified product have a particle size distribution meeting the preferred criteria of Example II (i.e., particles substantially entirely less than about 20 microns in diameter and predominantly less than about 4 microns in diameter, at least about 90% being less than about 15 microns in diameter.)

Subsequent grinding may be performed by any suitable grinding equipment such as an air mill, sand mill, ball mill, hammer mill or the like. Air milling procedures are especially preferred.

Subsequent grinding not only serves the cosmetic effect of reducing the particle size of the final product (which may agglomerates somewhat during the heating step), but it also improves the flame retardant utility by permitting more uniform dispersions of the agent in the polymer. Physical properties of the treated polymer are improved as well.

Moreover, subsequent grinding also serves to remove residual bromine that may remain after heating where the product of the initial grinding step contained significant numbers of particles more than 20 microns in diameter. In general, materials having 20-50 ppm bromine after the heating step can, by subsequent grinding in accordance with this invention, be brought to less than 20 ppm bromine.

EXPERIMENTAL EVALUATIONS

The ability of the process of this invention to yield purified decabromodiphenyl ether has been demonstrated on a laboratory scale as follows.

EXAMPLE V

Ground and unground crude decabromodiphenyl ether samples were placed in crystal dishes to a depth of about 1-2 centimeters and were subjected to heating for one hour at a temperature of about 250° C. in a forced air oven preheated to about 250° C. Bromine was determined prior and subsequent to heating by a melt analysis method described below.

A 100 gram sample of decabromodiphenyl ether was melted under vacuum, and the liberated bromine and other volatiles were collected in a liquid nitrogen trap. The trap was then allowed to warm to room temperature, and the evolved bromine was transferred to aqueous potassium iodide with a nitrogen purge. Free iodine generated by this operation was then titrated with sodium thiosulfate. The weight percent bromine in the original decabromodiphenyl ether sample may be determined by calculation.

Thermal stability of the ground and unground decabromodiphenyl ether samples was also observed after heating at 300° C. for 30 minutes. Thermal stability is based on a series of thermal stability standards in accordance with which 0 indicates no discoloration; X is slight discoloration (cream); XX is moderate discoloration (tan); and XXX is severe discoloration (dark bronw).

Table IV gives the foregoing data for the ground and unground samples and also gives the color of the purified product.

TABLE IV

Crude Decabromodiphenyl Ether Dried 1 Hour at 250° C.

| Sample Description | Particle Size | Bromine (ppm)** Unheated | Heated | Thermal Stability | Heated Color |
|---|---|---|---|---|---|
| Ground | "ground"* | 822 | 0 | X←XX | gray |
| Ground | 20%<5μ 70% 5-20μ 10% 20-40μ | 400 | 9 | X-XX | gray |
| Unground | 5%<20μ 35% 20-50μ | 813 | 378 | XX-XXX | tan |

TABLE IV-continued

Crude Decabromodiphenyl Ether Dried 1 Hour at 250° C.

| Sample Description | Particle Size | Bromine (ppm)** Unheated | Heated | Thermal Stability | Heated Color |
|---|---|---|---|---|---|
| | 25% 50-100μ | | | | |
| | 35% 100-200μ | | | | |

*Particle size distribution-unknown
**By vacuum melt method.

The foregoing data demonstrate the importance of grinding crude decabromodiphenyl ether to be purified by a time-temperature related heating step.

EXAMPLE VI

A 150 g. sample of Example IV (Unground) DBDPE was placed on a crystal dish and placed in a forced air oven at 275° C. for 4 hours. Residual free bromine values, as determined by the vacuum melt method, are given in Table V. These data demonstrate that even prolonged heating at 275° C. was incapable of purifying unground crude material.

TABLE V

Oven Heating of Unground DBDPE

| Time at 275° C. (Min.) | Free Bromine (ppm) |
|---|---|
| 0 | 402 |
| 60 | 263 |
| 240 | 194 |

EXAMPLE VII

The following example demonstrates the added advantage of grinding DBDPE to a high degree. Thermally stable decabromodiphenyl ether samples were prepared with high quality diphenyl oxide and bromine raw materials and were thoroughly ground on a well controlled basis to yield samples having the particle size, thermal stability, and unheated free bromine content shown in Table VI. Portions of these samples were placed in crystal dishes and were subjected to forced air oven heat at 200°, 216°, 230° and 250° C., respectively. The free bromine content, as measured by the vacuum melt method for each sample at each temperature, is given in Table VI and demonstrates an outstanding degree of bromine removal at temperatures throughout the 200°-250° C. range. The samples all exhibited excellent color after heating, and no significant color difference was seen for the products heated at the four different temperatures.

TABLE VI

| Sample Particle Size | Thermal Stability | Bromine (ppm) Unheated | Heated 1 hr. at 200° C. | 216° C. | 230° C. | 250° C. |
|---|---|---|---|---|---|---|
| 90%<5μ 10% 5-20μ | X | 260 | 20 | 18 | 7 | 2 |
| 85%<5μ 15% 5-20μ | X←XX | 292 | 29 | 20 | 10 | 3 |

EXAMPLE VIII

The efficacy of the process of this invention in purifying decabromodiphenyl ether has been demonstrated on a plant scale basis as shown in the following example. Using highly purified bromine and diphenyl oxide, decabromodiphenyl ether exhibiting a high level of thermal stability (X-XX) was prepared. Free bromine content of the crude product ranged between 200 and 300 ppm. This decabromodiphenyl ether was ground thoroughly in an air mill to yield a typical product with particles having 100% less than 20 microns, 90% less than 15 microns in diameter, and at least 50% less than 4 microns in diameter.

This crude ground decabromodiphenyl ether was introduced into the feed hopper of a rotary tray dryer. Air temperatures ranged from about 220°–260° C. inside the dryer, with product temperatures being slightly less at certain locations.

The color of the product after heating was off-white with little variation from drum to drum. The APHA color rating ranged from 10 to 20, with most samples having a value of 15–20 for a solution containing one gram of decabromodiphenyl ether in 100 milliliters of ethylene dibromide.

Final bromine values ranged from about 5–16 parts per million for 33 different product samples that were analyzed. Only eight of the 33 samples were in excess of 10 parts per million.

Bromide levels were reduced to 100 parts per million for nine product samples analyzed.

EXAMPLE IX

A series of oven studies was performed in order to demonstrate the precise time-temperature relationship needed for effective bromine removal. Three different particle size distributions were employed. The samples of crude DBDPE contained about 60–250 ppm bromine after grinding. Samples of each (150 g.) were placed in crystal dishes and subjected to oven heating at various temperatures throughout the temperature range for this invention. Residual free bromine levels were then measured at periodic intervals by the vacuum melt method described in Example V. These data are reported in TABLE VII.

TABLE VII
TIME-TEMPERATURE DATA

| DBDPE Sample | Time In Oven (Min) | Residual Bromine (ppm) At Various Temperatures | | | | | |
|---|---|---|---|---|---|---|---|
| | | 150° | 175° | 200° | 225° | 250° | 275° |
| Example I | 0 | | 252 | 252 | 331 | 252* | |
| | 2.5 | | | | | 145* | |
| | 5 | | | | 155 | 69* | |
| | 10 | | | 109 | 118 | 64* | |
| | 15 | | 169 | | 69 | | |
| | 20 | | | 90 | | 51* | |
| | 30 | | 135 | 78 | 69 | 46* | |
| | 45 | | | | 55 | | |
| | 60 | | 112 | 68 | | | |
| | 120 | | | | 43 | | |
| | 630 | | | | 28 | | |
| Example II | 0 | | 212 | 212 | 206 | 206 | 190 |
| | 3 | | | | | | 29 |
| | 4 | | | | | 35 | |
| | 5 | | | | 43 | | 60 |
| | 8 | | | | | 22 | |
| | 10 | | | | 31 | | 19 |
| | 15 | | | 56 | 26 | | |
| | 30 | | | 32 | 24*** | 16 | 8 |
| | 60 | | 69 | 32 | | 11 | |
| | 70 | | | | 18 | | |
| | 120 | | 42 | | | | |
| | 210 | | | | 16 | | |
| | 240 | | | 24 | | | |
| | 350 | | 36 | | | | |
| Example III | 0 | 70 | 115 | 70 | 90 | 120 | 60 |
| | 2 | | | | | 35 | |
| | 3 | | | | | | 12 |
| | 4 | | | | 7 | 10 | |
| | 5 | | | 48 | | | 7 |
| | 8 | | | | 7 | 3 | |
| | 10 | | | 23 | | | |
| | 15 | | 39 | 15 | 2** | 1 | |
| | 16 | | | | | | |
| | 30 | 44 | 25 | 3 | 4*** | | |
| | 60 | 31 | 6 | | 2**** | | |
| | 120 | 29 | | | | | |
| | 180 | 28 | | | | | |
| | 240 | 21 | | | | | |
| | 360 | 17 | | | | | |

*Heated at 255° C.
**Sample taken at 16 minutes
***Sample taken at 32 minutes
****Sample taken at 64 minutes On the basis of these data from Table VII, the time-temperature relationships necessary for practicing the invention may be determined. In this regard, the minimum heating time for a given temperature at which residual free bromine drops below about 20 ppm may generally be taken as minimum time necessary for effective purification.

The following Example demonstrates the benefits of the subsequent grinding step.

EXAMPLE X

Crude ground DBDPE of the type described in Example I was treated in a rotary tray dryer operated at the temperatures and in the manner described in Example VIII. The purified heated decabromodiphenyl ether obtained at the dryer outlet was found to have a free bromine content of 34 ppm.

This material was passed through an air mill to reduce the particle size distribution to the range given in Example II. The bromine level of the material after the subsequent grinding, as determined by the vacuum melt method, was 6 ppm, thus demonstrating that the final grinding step is effective in further reducing free bromine levels to acceptable levels.

EXAMPLE XI

By carefully controlling the purity of the raw material bromine and diphenyl oxide employed in producing decabromodiphenyl ether, product of the desired thermal stability (X-XX or better) may routinely be obtained. The substantial exclusion of aliphatic and alicyclic hydrocarbon containing impurities has been found to be essential in producing decabromodiphenyl ether of the desired thermal stability.

The following simple procedure may be used to prepare purified bromine for use in accordance with this invention. Production bromine containing relatively high levels of oily hydrocarbon impurities, chloroform, and carbon tetrachloride was placed in a suitable reaction vessel containing aluminum chloride. After reaction, the mixture was fractionally distilled, with bromoform, carbon tetrabromide and the high boiling oils being retained in the pot and purified bromine collected overhead.

EXAMPLE XII

Aliphatic and alicyclic hydrocarbon groups are generally and customarily found as impurities at varying levels in a number of the grades of diphenyl ether commercially available on the open market. In the course of the work leading to the development of the subject process, a study was made of commercially available diphenyl ether samples. Decabromodiphenyl ether, which had been prepared from the ether samples to be evaluated and bromine that had been highly purified by fractional distillation, was hand ground and heated at 300° C. for 30 minutes to determine its thermal stability. Table VIII reports data obtained for evaluations of various lots of commercial diphenyl ether samples. Table VIII also includes data for material prepared using a preferred diphenyl ether purified by two fractional crystallizations, which has been taken as the reference standard with which other results are compared.

As previously noted, dibenzofuran and dibenzodioxin are frequent diphenyl ether impurities. The presence of such impurities appears to be one source of purity problems in perbrominated products produced therefrom. Using vapor phase chromotography (VPC) techniques, the foregoing commercial diphenyl ether samples were analyzed for dibenzofuran and dibenzodioxin, and these results are reported in Table IX. As noted, in comparison with the preferred material and a perfume grade diphenyl ether, other commercial diphenyl ethers exhibit varying quantities of these undesirable impurities.

EXAMPLE XIII

One method of measurement of bromine quality is obtained from infrared spectra of samples. From the infrared spectra there are identified a number of potential bromine impurities. Table X gives the identities of a number of impurities noted through IR absorbance.

Using the purified diphenyl ether (Sample No. 1) as the reference standard, bromine from a variety of sources was used to produce decabromodiphenyl ether, samples of which were subjected to thermal stability testing using the previously described technique. Table XI reports data for bromine from various sources. These data demonstrate that only the distilled bromine, from which the impurities present in commercially available bromine have been removed, produced the desired level of thermally stable decabromodiphenyl ether. Table XI also identifies impurities observed from IR spectra.

Based on the foregoing work, it appears that aliphatic and alicyclic hydrocarbon group containing impurities are typically found in commercial grades of diphenyl ether and bromine.

TABLE VIII

Diphenyl Ether Quality - Commercial Samples

| Sample No. | | Thermal Stability 300° C./30 min. |
|---|---|---|
| 1. (Supplier A) | Purified by 2 fractional crystallizations | X |
| 2. (Supplier B) (Perfume Grade) | | X |
| 3. (Supplier C) | | X |
| 4. (Supplier C) | | X |
| 5. (Supplier C) | | X←XX |
| 6. (Supplier D) | | X |
| 7. (Supplier D) | | X←XX |
| 8. (Supplier D) | | X←XX |
| 9. (Supplier D) | | X←XX |
| 10. (Supplier E) | | X←XX |
| 11. (Supplier E) | | X←XX |
| 12. (Supplier E) | | X←XX |
| 13. (Supplier E) | | X←XX |
| 14. (Supplier E) | | X←XX |
| 15. (Supplier E) | | X←XX |

TABLE IX

Dibenzofuran and Dibenzodioxin in Commercial Diphenyl Ethers (VPC Assay)

| Sample No. | Dibenzofuran, ppm | Dibenzodioxin, ppm |
|---|---|---|
| 1. | Not detected | Not detected |
| 2. | Not detected | Not detected |
| 3. | Trace (20–50 ppm?) | Not detected |
| 4. | Trace (20–50 ppm?) | Not detected |
| 5. | 8 sample ranged 500–2000 ppm | Not detected in 7 sample, slight trace in one |

TABLE X

Identification of Common Bromine Impurities

| Impurity | Infrared, cm$^{-1}$ (Relative Intensity) |
|---|---|
| Water, $H_2O$ | 3680 (strong), 3590 (strong), 1590 (strong) |
| Hydrocarbons | Multiple peaks between 2850–3000, three main peaks at ~2860 (medium), 2930 (strong), and 2960 (strong). Secondary oil peaks are found as a broad band at 1400–1470 (medium). |
| Hydrogen Chloride, HCl | A single broad peak centered at ~2800. |
| Hydrogen Bromide, HBr | A single broad peak centered at ~2480. |
| Carbon Dioxide, $CO_2$ | A single, sharp peak at 2350. |
| Carbonyl, $-\overset{O}{\underset{\|}{C}}-$ (the identity of this impurity(s) is unknown, usually composed of both volatile and nonvolatile components) | Broad band ~1680–1780. |
| Chloroform, $CHCl_3$ | 1210 (weak), 760–770 (strong) |
| Carbon Tetrachloride, $CCl_4$ | A double peak at 785 (strong) and 760 (medium strong). Note that the 760 peak will be masked in the presence of $CHCl_3$, chloroform. |
| Bromoform, $CHBr_3$ | ~3030 (weak), 1145 (medium strong), 660 (strong) |
| p-Dibromobenzene | 805 (strong), 1005 (strong), 1065 (strong), 1380 (medium) 1470 (strong). |
| Sulfuric Acid, $H_2SO_4$ | A series of three broad bands centered at 1150–1200 (strong), 1050 (medium strong), and 880–900 (medium). |

TABLE XI

Bromine Quality - Effect on Thermal Stability Decabromodiphenyl Ether Prepared with Purified Diphenyl Ether (Sample 1, Table VIII)

| Sample Number | Hydrocarbon Peak IR Absorbance | Other Impurities | Thermal Stability |
|---|---|---|---|
| 1. | Nil | — | X |
| 2. | Nil | — | X |
| 3. | Nil | — | X |
| 4. | 0.02 | — | X←XX |
| 5. | 0.087 | — | X-XX |
| 6. | 0.089 | — | X-XX |
| 7. | 0.13 | Low | XX |
| 8. | 0.44 | — | XX?? |
| 9. | 0.72 | Low | XXX |
| 10. | Very high organics | | 4X |

TABLE XI-continued

Bromine Quality - Effect on Thermal Stability Decabromodiphenyl Ether Prepared with Purified Diphenyl Ether (Sample 1, Table VIII)

| Sample Number | Hydrocarbon Peak IR Absorbance | Other Impurities | Thermal Stability |
|---|---|---|---|
| | | | (black) |
| 11. | Nil | Low | X |
| 12. | Nil | Moderate | X←XX |
| 13. | 0.51 | Moderate | |
| | 0.079 | High CHBr$_3$ | XX-XXX |
| 14. | Nil | 1000 + ppm CHBr$_3$ | XX |
| 15. | Nil | 200 ppm CHBr$_3$ | XX |
| 16. | Nil | 500–1000 ppm CHBr$_3$ | X←XX |
| 17. | Nil | 2000 ppm CHBr$_3$ | X→XX |
| 18. | Nil | 1500 ppm CHCl$_3$ | XX-XXX |

EXAMPLE XIV

Thermally stable decabromodiphenyl ether may be obtained using purified raw materials of the foregoing type by direct bromination of diphenyl oxide in a 125% excess of bromine without other reaction solvent and employing a bromination catalyst such as aluminum metal, iron, and iron and aluminum halides. Aluminum chloride is the preferred catalyst as shown in this example.

Bromine, 350 g. (2.18 mole), was charged into a 250 ml flask fitted with mechanical stirrer, addition funnel with pressure equalizing side arm, and condenser. The vent from the condenser led to a water trap which was used to collect evolved hydrogen bromide. Anhydrous aluminum chloride, 0.83 g. (0.0062 mole), was added to the bromine and the mixture stirred 15 minutes while warming to approximately 45° C. Diphenyl oxide, 16.5 g. (0.097 mole), was then added dropwise over a period of 30–45 minutes. The reaction mixture was then heated and maintained at reflux until HBr evolution ceased—a period of 1–2 hours.

After cooling to 30° C., 125 ml. water was added. The apparatus was set up for distillation by removing the addition funnel and reflux condenser, then adding a distilling head with condenser and 100 ml receiver. A thermometer was added to measure pot temperatures. Heat was applied and the excess bromine distilled off. Crude product was filtered, washed with water, and dried in a forced air oven at 100° C. Theoretical yield of decabromodiphenyl ether for this size reaction is 93.2 g.

EXAMPLE XV

A series of experimental runs were performed in order to determine the effect of raw material quality on the thermal stability of crude, unpurified decabromodiphenyl ether. In each case, decabromodiphenyl ether was prepared by reacting diphenyl oxide in an excess of bromine without further reaction solvents in the presence of anhydrous aluminum chloride as a bromination catalyst as disclosed in Example XIV.

After recovery of the crude decabromodiphenyl ether, a sample of the material was maintained at 300° for 30 minutes, and the resulting color observed and in accordance with the thermal stability standards set forth in Example VII. Several bromine sources were employed. The highest purity was exhibited by production bromine which was fractionally distilled and contained no aliphatic or alicyclic hydrocarbon impurities and exhibited low levels of chloroform and carbon tetrachloride. A second source of bromine was a production bromine having low to moderate levels of hydrocarbon contamination. A third source of bromine was production bromine exhibiting moderate to high levels of hydrocarbon contamination. A final source of bromine was production bromine containing the bottoms from a bromine tower non-volatile residue column which exhibited high levels of hydrocarbon contamination. In all cases commercial technical grade diphenyl oxide was employed. The highest level of purity was obtained by purifying this technical grade diphenyl oxide by three fractional crystallizations. The unpurified technical grade diphenyl oxide consisted of the mother liquor from the fractional crystallization containing concentrated diphenyl oxide impurities.

Using various combinations of these raw materials, six experimental preparations of decabromodiphenyl ether were carried out, and the thermal stability of the unpurified crude product was thereafter obtained in the manner described. These data are reported in Table XII.

TABLE XII

Effect of Raw Material Quality on Thermal Stability of Decabromodiphenyl Ether

| Run No. | Bromine | Diphenyl Oxide | Thermal Stability of Unpurified Product |
|---|---|---|---|
| 1. | Purified[1] | Purified[2] | X |
| 2. | Unpurified[3] | Purified[2] | X-XX |
| 3. | Unpurified[4] | Purified[2] | XX-XXX |
| 4. | Purified[1] | Unpurified[5] | XXX |
| 5. | Unpurified[6] | Purified[2] | XXX |
| 6. | Unpurified[6] | Unpurified[5] | XXXX (Black) |

[1]Distilled production bromine containing no aliphatic or alicyclic hydrocarbons, low levels of CHCl$_3$ and CCl$_4$.
[2]Technical grade commercial diphenyl oxide purified by 3 fractional crystallizations.
[3]Production bromine containing low to moderate levels of hydrocarbon contaminants.
[4]Production bromine containing moderate to high levels of hydrocarbon contaminants.
[5]Mother liquor from fractional crystallizations of technical grade commercial diphenyl oxide.
[6]Production bromine containing high levels of hydrocarbon contaminants.

As can be seen, only in the case of Run No. 1, which employed purified bromine and purified diphenyl oxide, was the high thermal stability material obtained. In all other cases, even where one or the other of the raw materials was purified, unsatisfactory thermal stabilities were observed. In the case of Run 6, employing highly impure bromine and diphenyl oxide, the resulting product was so unstable as to exhibit a level of discoloration (XXXX-Black) beyond that normally observed.

By employing diphenyl oxide and bromine that are substantially free of aliphatic and alicyclic hydrocarbon groups a thermally stable crude decabromodiphenyl ether is obtained which, when ground and heated in accordance with this invention, provides a purified decabromodiphenyl ether of consistent high quality.

EXAMPLE XVI

A series of experiments was performed to compare the efficacy of the technique of this invention with the closest known prior art purification methods. Following the procedure disclosed in Example 1 of Burk U.S. Pat. No. 3,733,366, decabromobiphenyl was prepared. Aluminum chloride catalyst (2.5 g.), biphenyl (38.5 g., 0.25 mole) and methylene chloride (500 ml) were charged to a one liter, four neck flask equipped with reflux condenser, HBr trap, pot thermometer, stirrer and bromine addition funnel. The mixture was cooled to 7° C., and 355 ml of bromine (7.3 moles) were added at 3°–7° C. over a two hour period. The temperature was then increased to 43°–44° C. for an additional 3½ hours. The reaction mass was transferred to a 4 liter Erlenmeyer flask, and 25 ml. of concentrated hydrochloric acid and 200 ml. of water were added. Excess bromine was neutralized by adding sodium hydrogen sulfite solution. The product was suction filtered, washed with water and air dried overnight on a Teflon tray. The air dried material was heated at 140° C. for 72 hours in a forced air oven. Residual bromine was determined by the vacuum melt method described in Example I herein.

Decabromodiphenyl ether was also prepared using the same method of preparation and purification of Example 1 of Burk U.S. Pat. No. 3,733,366. After the purification step (heating at 140° C. for 72 hours), the product was visually observed, and residual bromine was measured by the vacuum melt method.

Decabromodiphenyl ether was prepared following the procedure of Example VI of Stepniczka U.S. Pat. No. 3,965,197. To a 500 ml. four neck flask equipped with a mechanical stirrer, a reflux condenser, a pot thermometer, an HBr trap and a bromine addition funnel, was charged 150 ml. of bromine (2.93 moles). To a second bromine increment 101 ml. (1.97 moles) of the total of 782 g. of bromine was added about 0.5 g. aluminum (sufficient aluminum to provide 5 grams of aluminum bromide in solution). The reaction flask was cooled to about 10° C., and 34 g. (0.2 moles) of diphenyl oxide were added in small amounts to the bromine. After all of the diphenyl oxide had been added, the second portion of bromine containing aluminum bromide was added to it. The temperature of the mixture was then allowed to rise to reflux and was held there for about four hours. The excess bromine was removed by blowing superheated steam through the reaction vessel and collecting the bromine in an outside vessel. An orange-peach colored product was obtained, filtered, washed with 500 ml. water and dried in an oven at 100° C. for one hour. Residual bromine was determined by the vacuum melt method.

Following the procedure disclosed in Example IV of Nagy et al. U.S. Pat. No. 3,752,856, decabromodiphenyl ether was prepared. The mixer employed was a 1 quart working capacity sigma blade mixer obtained from Teledyne-Readco equipped with a 1 horsepower electric motor. Attached to the mixer were a bromine addition funnel and two double wall reflux condensers that were in communication with an HBr trap which was mounted on a weight balance in order to monitor HBr evolution. A recirculatng water bath, capable of heating or cooling, was in connection with the mixer jacket to maintain the disclosed reaction temperature(s).

Into the clean and dry mixer were charged 102 g. diphenyl oxide (0.6 mole) and 2.4 g. anhydrous aluminum chloride. Bromine addition was immediately commenced at a rate of 500 g. per hour, which after one hour was reduced to 250 g. per hour. Reaction temperature during the first two hours of bromine addition was maintained at 20°–25° C., and then was raised to 50° C. for the remainder of the bromine addition. Bromine addition was again reduced after the second hour to 190 g. per hour and continued until a total of 1036.7 g. (6.48 mole) of bromine had been added. Total bromine addition time was 3 hours, 50 minutes. After the bromine addition was complete the reaction temperature was raised to 64° C. and held for 90 minutes, at which time hydrogen bromide evolution had ceased. Titration of the HBr trap for bromine revealed that 73.9 g. (0.46 mole) of bromine were carried overhead and therefore that 962.8 g. (6.02 moles) of bromine were available for reaction in the mixer, a 0.33 percent excess of bromine. A vacuum (21 mm. Hg) was then applied to the apparatus and the system was flushed with dry air. The system was then cooled to ambient temperature, normal pressure restored, and purged with 29 g. anhydrous gaseous ammonia during a period of 18 minutes. A brown-gray product weighing 548.1 g. was obtained. Several large chunks were dark gray inside. Only 65 percent of the product as obtained would pass through an eighteen mesh (1.0 mm opening) screen. The material smaller than 1 mm was further examined by microscope and found to be 10% greater than 500μ, 80% 100–500μ, and 10% less than 100μ. A brown-gray colored product was obtained that melted at 271°–87° C. Residual bromine was determined by the vacuum melt method.

The visual appearance and the experimentally determined residual bromine levels are given in Table XIII for the experimentally prepared versions of the products of Burk, Stepniczka and Nagy et al patents. For comparative purposes, Table XIII also gives the free bromine levels and visual appearance for decabromodiphenyl ether produced on a plant scale in accordance with the process of this application, as previously given in Example VIII, as well as the measured free bromine level for the unground DBDPE of Example IV after heating at 275° C. for 4 hours as reported in Example VI.

TABLE XIII

| Product | Method of Preparation | Free Bromine Level (PPM) | Visual Appearance |
|---|---|---|---|
| Decabromobiphenyl | Example 1 of Burk U.S. Pat. No. 3,733,366 | 517 | Buff |
| Decabromodiphenyl ether | Example 1 of Burk U.S. Pat. No. 3,733,366 | 153 | Lt. Tan |
| Decabromodiphenyl ether | Example VI of Stepniczka U.S. Pat. No. 3,865,197 | 1065 | Orange/Peach |
| Decabromodiphenyl ether | Example IV of Nagy et al. U.S. Pat. 3,752,856 | 488 | Brown/gray |
| Decabromodiphenyl ether | Invention Process (Example VIII) | 5–16* | Off-White |
| Decabromodiphenyl ether | Unground (Example VI) | 194 | — |

*Range of values for 33 samples.

As may readily be perceived from the data of Table XIII, the purification process of the present invention yields decabromodiphenyl ether having exceedingly low residual bromine levels (in the range of 6–16 ppm) and having a highly acceptable off-white color. The processes of the prior art do not yield acceptably pure products. Thus, in the case of Stepniczka, a bromine level in excess of a thousand parts per million and a highly unacceptable orange-peach color are observed. Likewise, replication of Example I of the Burk patent produces buff colored decabromobiphenyl containing 517 ppm bromine. Decabromodiphenyl ether produced in accordance with the Burk process has a free bromine level of 153 (ten times higher than the levels obtained with this invention) and an unacceptable light tan coloration. With Nagy et al., the decabromodiphenyl ether produced was an undesirable brown-gray color and exhibited free bromine at a level of 488 ppm, and heated but unground material is likewise wholly unsatisfactory.

Although described in detail and especially useful for use with decabromodiphenyl ether, the method of this invention may also be employed with other grindable brominated aromatic compounds that contain occluded bromine and hydrogen bromide and that remain thermally stable solids under the conditions of treatment. Thus, this invention may be employed with materials such as pentabromophenol, decabromodiphenyl sulfide, decabromodiphenylamine and the like. As will be obvious to those skilled in the art, the particular choice of heating times and temperatures and particle size will vary from compound to compound.

We claim:

1. A process for purifying crude solid decabromodiphenyl ether containing occluded bromine and hydrogen bromide as impurities comprising the steps of:
   grinding the crude decabromodiphenyl ether to provide particles predominantly less than about 20 microns in diameter and substantially entirely less than about 100 microns in diameter; and
   subsequently heating the crude ground decabromodiphenyl ether at a temperature of about 150°–300° C. for a time sufficient to effect substantial removal of the impurities therefrom.

2. A process for preparing purified thermally stable decabromodiphenyl ether comprising the steps of:
   reacting diphenyl oxide in an excess of bromine without other reaction solvents in the presence of a bromination catalyst, the diphenyl oxide and bromine being substantially free of impurities containing aliphatic and alicyclic hydrocarbon groups, the diphenyl oxide containing no more than about 5000 ppm dibenzofuran and 2-phenylphenol, and the bromine being substantially free of chloroform and carbon tetrachloride;
   recovering the crude thermally stable decabromodiphenyl ether thereby produced;
   grinding the crude decabromodiphenyl ether to provide particles predominantly less than about 20 microns in diameter and substantially entirely less than about 100 microns in diameter; and
   subsequently heating the crude ground decabromodiphenyl ether at a temperature of about 150°–300° C. for a time sufficient to effect substantial removal of the impurities therefrom.

3. A process, as claimed in claim 2, wherein the bromine is purified by distillation prior to reaction with the diphenyl oxide.

4. A process, as claimed in claim 2, wherein the bromine is treated with a member selected from the group consisting of aluminum and aluminum chloride prior to distillation.

5. A process for preparing thermally stable decabromodiphenyl ether comprising the steps of:
   reacting diphenyl oxide in an excess of bromine without other reaction solvents in the presence of a bromination catalyst, the diphenyl oxide and bromine being substantially free of impurities containing aliphatic and alicyclic hydrocarbon groups, the diphenyl oxide containing no more than about 500 ppm dibenzofuran and 2-phenylphenol and the bromine being substantially free of chloroform and carbon tetrachloride; and
   recovering the thermally stable decabromodiphenyl ether thereby produced.

6. A process, as claimed in claim 5, wherein the bromine is purified by a distillation prior to reaction with the diphenyl oxide.

7. A process, as claimed in claim 6, wherein the bromine is treated with a member selected from the group consisting of aluminum and aluminum chloride prior to distillation.

8. A process, as claimed in claim 5, wherein the thermally stable decabromodiphenyl ether is ground to provide particles predominantly less than about 20 microns in diameter and substantially entirely less than about 100 microns in diameter and is thereafter heated at a temperature of about 150°–300° C. for a time sufficient to effect substantial removal of the impurities therefrom.

9. A process, as claimed in claim 1, 2, or 8, wherein the crude ground decabromodiphenyl ether is heated for about 2 minutes to 4 hours.

10. A process, as claimed in claim 9 wherein the crude ground particles are substantially entirely less than about 20 microns in diameter, at least about 90% of the particles being less than about 15 microns in diameter and the particles being predominantly less than about 4 microns in diameter.

11. A process, as claimed in claim 9, wherein the crude ground decabromodiphenyl ether is heated at a temperature of about 200°–275° C. for about 5–60 minutes.

12. A process for purifying crude solid, decabromodiphenyl ether containing occluded bromine and hydrogen bromide as impurities comprising the steps of:
   grinding the crude decabromodiphenyl ether to provide particles substantially entirely less than about 20 microns in diameter, at least about 90% of the particles being less than about 15 microns in diameter and the particles being predominantly less than about 4 microns in diameter; and
   subsequently heating the crude ground decabromodiphenyl ether for about 10–45 minutes at a temperature of about 210°–260° C. in order to effect substantial removal of the impurities therefrom.

13. A process, as claimed in claim 12, wherein the crude decabromodiphenyl ether is prepared by reacting diphenyl oxide in an excess of bromine without other reaction solvents in the presence of bromination catalyst.

14. A process, as claimed in claim 13, wherein the decabromodiphenyl ether is thermally stable.

15. A process for purifying crude solid decabromodiphenyl ether containing occluded bromine and hydrogen bromide impurities comprising the steps of:
   grinding the crude decabromodiphenyl ether to provide particles substantially entirely less than about 15 microns in diameter, at least about 90% of the particles being less than about 5 microns in diameter and the particles being predominantly less than about 3 microns in diameter; and subsequently heating the crude ground decabromodiphenyl ether for about 2 minutes to 4 hours at a temperature of about 150°–300° C. in order to effect substantial removal of the impurities therefrom.

16. A process, as claimed in claims 1, 2, 8, 12, or 15, and comprising the further step of subsequently grinding the purified heated decabromodiphenyl ether to provide particles substantially entirely less than about 20 microns in diameter, at least about 90% of the particles being less than about 15 microns in diameter and the particles being predominantly less than about 4 microns in diameter.

* * * * *

UNITED STATES PATENT AND TRADEMARK OFFICE
CERTIFICATE OF CORRECTION

PATENT NO. : 4,327,227

DATED : April 27, 1982

INVENTOR(S) : James T. Ayres, et al.

It is certified that error appears in the above-identified patent and that said Letters Patent are hereby corrected as shown below:

Column 5, line 39, "to" should be --and--.

Column 9, line 53, "bronw)." should be --brown).--.

Column 15, line 60, "300°" should be --300°C.--.

Column 15, line 63, "VII" should be --VIII--.

Column 15, line 68, "bromine was" should be --bromine employed was--.

Column 19, line 4, "decabromobiphenyl" should be --decabromodiphenyl--.

Column 20, line 4, "500" should be --5000--.

Column 20, line 11, "by a distillation" should be --by distillation--.

Column 20, line 56, "of bromination" should be --of a bromination--.

Signed and Sealed this

Seventeenth Day of August 1982

[SEAL]

Attest:

GERALD J. MOSSINGHOFF

Attesting Officer  Commissioner of Patents and Trademarks